United States Patent [19]

Evans et al.

[11] Patent Number: 5,432,074
[45] Date of Patent: Jul. 11, 1995

[54] FORMULATION FOR TREATING SILAGE CONTAINING β-1,4-XYLANASE AND β-1,3-XYLOSIDASE BUT ESSENTIALLY FREE OF β-1,4-GLUCANASE AND β-1,4-CELLOBIOHYDROLASE, AND ONE OR MORE LACTIC ACID-PRODUCING BACTERIA

[75] Inventors: Christopher T. Evans, Heydon; Stephen P. Mann, Harston; Robert C. Charley, Cardiff; David Parfitt, Pontypool, all of United Kingdom

[73] Assignee: Biotal Ltd., Cardiff, United Kingdom

[21] Appl. No.: 75,516

[22] PCT Filed: Dec. 16, 1991

[86] PCT No.: PCT/GB91/02246

§ 371 Date: Aug. 13, 1993

§ 102(e) Date: Aug. 13, 1993

[87] PCT Pub. No.: WO92/10945

PCT Pub. Date: Jul. 9, 1992

[30] Foreign Application Priority Data

Dec. 17, 1990 [GB] United Kingdom ............... 9027303

[51] Int. Cl.6 ............ A23B 7/10; C12N 9/24; C12N 9/26; C12N 9/38
[52] U.S. Cl. ................... 435/200; 426/50; 426/52; 426/53; 435/99; 435/201; 435/207; 435/208
[58] Field of Search .......... 435/183, 162, 163, 164, 435/165, 200, 99, 201, 207; 426/50, 52, 53

[56] References Cited

U.S. PATENT DOCUMENTS

| 3,147,121 | 9/1964 | Brown | 426/53 |
| 4,342,786 | 8/1982 | Raccach | 426/52 |
| 5,002,778 | 3/1991 | Grant | 426/53 |

FOREIGN PATENT DOCUMENTS

| 0468596 | 1/1992 | European Pat. Off. |
| 1223940 | 3/1971 | United Kingdom . |
| 1584710 | 2/1981 | United Kingdom . |
| 1591810 | 6/1981 | United Kingdom . |
| WO91/15966 | 10/1991 | WIPO . |

OTHER PUBLICATIONS

Bonhomme-Florentin, British Journal of Nutrition, 1988, 60, 185–192.

M. Coughlan, "Enzyme Systems for Lignocellulose Degradation", *Elsevier Applied Science*, pp. 347–355, 1989.

K. Poutanen et al., "Evaulation of Different Microbial Xylanolytic Systems", *Journal of Biotechnology*, vol. 6, No. 1, p. 49, Jul. 1987.

Z. G. Weinberg et al., "Recovery of Protein and Chlorophyll from Alfalfa by Simultaneous Lactic Acid Fermentation and Enzyme Hydrolysis (ENLAC)", *Enzyme and Microbial Technology*, vol. 12, No. 12, pp. 921–925, Dec. 1990.

S. Bolenz et al., "Treatments of Water Hyacinth Tissue to Obtain Useful Products", *Biological Wastes*, vol. 33, No. 4, pp. 263–274, 1990.

C. M. Willis et al., "Influence of Sodium Hydroxide and Enzyme Additions on Nutritive Values of Rice Straw", *Journal of Animal Science*, vol. 50, No. 2, 1980, pp. 303–308.

J. R. Frederick et al., "Utilization of Agricultural Wastes—the Enzymic Breakdown of Hemicellulose", –Chemical Abstracts, vol. 92, No. 23, Jun. 9, 1990, Abstract No. 193303g.

*Primary Examiner*—David M. Naff
*Assistant Examiner*—Michael V. Mellar
*Attorney, Agent, or Firm*—Oliff & Berridge

[57] ABSTRACT

A formulation consisting essentially of -1,4-xylanase and -1,3-xylosidase, but essentially free of -1,4-glucanase and -1,4-cellobiohydrolase and on or more lactic acid-producing bacteria is disclosed. The formulation can be used in a silage composition to stabilize silage from cereal and other crops and to enhance its nutritive value and digestibility in a ruminant or other animal.

6 Claims, No Drawings

FORMULATION FOR TREATING SILAGE CONTAINING β-1,4-XYLANASE AND β-1,3-XYLOSIDASE BUT ESSENTIALLY FREE OF β-1,4-GLUCANASE AND β-1,4-CELLOBIOHYDROLASE, AND ONE OR MORE LACTIC ACID-PRODUCING BACTERIA

FIELD OF THE INVENTION

This invention relates to a formulation of enzymes and microorganisms and to its use in the treatment, e.g. enhancement of nutritive value, of silages made from annual crops, in particular maize and other crops ensiled with a relatively high dry matter, but also other crops such as lucerne and lays of perennial grasses.

BACKGROUND OF THE INVENTION

It has become increasingly common for farmers to ensile crops using biological additives. These commonly comprise enzymes designed to release sugars from cellulose, to promote the fermentation by naturally-occurring organisms, or microbial inoculants which use endogenous sugars, again to promote the production of lactic acid by fermentation. In some instances, a combination of the two technologies has been used.

Weinberg et al, Enzyme Microb. Technol. 12 (1990) 921–925, describe the simultaneous lactic acid fermentation and enzyme hydrolysis by cell wall-degrading enzymes, in order to recover protein from alfalfa. The preferred formulation contained mainly hemicellulases, cellulases and pectinases. It is hypothesised "that the synergistic action of enzymes and lactic acid bacteria removes a considerable portion of hemicellulose and other polysaccharides from the plant cell wall, increasing its permeability for cell content recovery."

Bolenz et al, Biological Wastes 33 (1990) 263–274, describe the use of pectinase/cellulase in order to solubilise the protein in water hyacinth. Lactofermentation is described as a "prerequisite for silage production" but requires the addition of sugar and the suppression of mould growth. Once again, the intention is to extract protein.

Willis et al, J. Animal Science 50 (2) (1980) 303–308, describe the addition of sodium hydroxide and enzymes to rice straw, in order to improve its nutritive value. The enzymes comprised hemicellulase, pectinase and β-glycosidase. The data relating to ensiled materials indicate that sodium hydroxide increases, while the enzymes decrease, dry matter digestibility.

Jorgensen et al, "Enzyme Systems for Lignocellulose Degradation", ed. Coughlan, pub. Elsevier (1989) 347–355, describe the use of hemicellulase to produce fermentable sugars such as xylose, arabinose and glucose in ensiled material for use as animal feedstuff. Although it is suggested that cellulose degradation may weaken the structure of the grass and cause drainage from a silo, the recommended formulation comprises "a cellulose complex consisting of endo- and exo-activities and including β-glucosidase (cellobiase)" in order to maximise the production of fermentable glucose and minimise structural disruption in the cell walls. The conclusion states that there is "continuing lack of knowledge about substrate composition, enzyme complexity and all of the other parameters crucial for occurrence of enzyme effect."

Commonwealth Agricultural Bureaux, Abstract 870701129, OG57-01979, reports that six enzyme preparations were tested on substrates including maize. It is suggested that enzyme formulations for degrading plant cell walls should be composed of hemocellulases and pectinases rather than cellulases.

GB-A-1591810 discloses the preservation of vegetables using a combination of bacteria and enzymes. The bacteria should be capable of both degrading higher carbohydrates into fermentable sugars and also of causing the fermentation of such sugars into lactic acid. The enzymes should be capable of breaking down carbohydrates, and in particular cellulose, starch and pentosans. Amylase, amyloglucosidase and hemicellulase are used, the latter defined as comprising galactomannase, pectinase, β-glucanase, xylanase and cellulase.

SUMMARY OF THE INVENTION

A novel formulation comprises one or more selected microorganisms and two or more enzymes characterised by the ability to degrade non-cellulosic polysaccharides as found in legumes or Gramineae. These enzymes comprise at least β-1,4-xylanase and β-1,3-xylosidase, but substantially free of β-1,4-glucanase and β-1,4-cellobiohydrolase. Such a formulation can be used to prepare material being ensiled, so that the material has enhanced stability, digestibility and nutritive value. At the same time, pentosans are produced that may be utilised by the selected microorganisms, to give a rapid production of lactic acid and thus a good fermentation of suitable palatability.

DESCRIPTION OF THE INVENTION

The invention is based on the observation that the complex non-cellulosic polysaccharide of Gramineae consist of a multitude of sugars linked by a variety of linkages. Thus, as reported by Medcalf (1985) and as shown in formula I (below), the non-cellulosic polysaccharide of corn (maize) bran consists of xylose, arabinose, galactose and glucuronic acid linked in various ways on a xylose backbone.

Maize is an example of a crop having a relatively high dry matter content, i.e. within the range 25 to 40% by weight. The invention is well adapted to use with such materials and also crops such as rye grass which have a relatively low dry matter content, e.g. between 12 and 25% by weight, and often 18 to 22% by weight. Like maize, rye grass has a high content of arabinoxylans.

Similar molecules to that of formula I are present in all Gramineae, although the composition may vary depending on the species in question and on the state of development. In some cases, glucose and mannose may be included, and in the legumes such as lucerne, there is a likelihood that polymers of galactose and mannose will predominate.

These polymers are part of a matrix of polysaccharides that is an integral part of the structural polysaccharides of plant cells, providing linkage between and around the cellulose molecules. The hydrolysis of these molecules can only be achieved by a combination of enzymes that recognise the various linkages between the sugars. Thus, for example, 2, 3, 4, 5, 6, 7, 8, 9, 10, 11, 12 or all 13 of the enzymes listed in Table 1, in combination (including the two essential enzymes), will achieve such hydrolysis and, in so doing, will open the cell wall polysaccharide complex while releasing the sugars for fermentation.

TABLE 1

| Enzyme | EC No. |
| --- | --- |
| β-1,4-xylanase | 3.2.1.8 |
| β-1,3-xylosidase | 3.2.1.72 |
| β-1,4-xylosidase | 3.2.1.37 |
| xylan endo-1,3β-xylosidase | 3.2.1.32 |
| α-L-arabinofuranosidase | 3.2.1.55 |
| β-1,3-arabinosidase | 3.2.1.88 |
| α-galactosidase | 3.2.1.23 |
| β-1,4-galactosidase | 3.2.1.89 |
| β-glucuronidase | 3.2.1.32 |
| α-amylase | 3.2.1.1 |
| polygalacturonase | 3.2.1.15 |
| pectin esterase | 3.1.1.11 |
| pectin lyase | 4.2.2.10 |

Among those listed in Table 1, preferred enzymes for use in the invention (in addition to the two essential enzymes) are β-1,3-arabinosidase and α-L-arabinofuranosidase. By way of example, the latter has the effect of removing the predominant side chain in sugars of formula I. Pectinase activity (i.e. the last 3 enzymes listed in Table 1) is desirable if the crop to be ensiled has been harvested at a time when the pectin content is high. Amylase is also often preferred, especially for use with alfalfa and clover/grass mixtures.

The inclusion of enzymes attacking cellulose, such as β-1,4-cellobiohydrolase, can cause, over a period of time, a complete breakdown of the plant cell material. The presence of these enzymes in any substantial quantities is therefore avoided.

Microorganisms for use in the present invention are selected for their ability to convert pentosans to lactic acid, without degrading protein, at a pH in the range 4-6.5. They will of course also be selected according to conventional criteria, having regard to their use, i.e. for quick growth and temperature competence, and preferably also for their inability to ferment organic acid. This last selection may not be necessary as such, but it is of course desirable to avoid losing the desired lactic acid.

Many bacteria will convert both 5- and 6-carbon sugars to lactic acid. The conversion of glucose and other 6-carbon sugars is, theoretically at least, more efficient, since one molecule of substrate is converted to two molecules of lactic acid, without any other carbon-containing product. However, by use of selected microorganisms in accordance with the present invention, in circumstances where pentosans are a readily-available substrate owing to the associated enzymatic activity, those microorganisms will proliferate.

It has been found that a single microorganism can satisfactorily act over a pH range of, say, 4.5-7.0. This is sufficient for the purposes of ensiling maize or another crop having a high dry matter content. When the dry matter content is lower, e.g. when the crop is rye grass, the pH of the ensiled material should drop to a lower level, e.g. 3.5-4. In these circumstances, it is preferred to include a second microorganism adapted to function at a lower pH than the first. Suitable genera of microorganisms for these purposes are Pediococcus and Lactobacillus respectively exhibiting maximum growth at pH 4.5-7.0 and pH 3.5-5.

The effect of the removal of some sugars of the non-cellulosic polysaccharides will cause the pH to drop, thus increasing the enzyme activities which have optimal activity in the region of pH 4-5. The nutritive value of the sugars will be largely maintained as lactic acid, providing that this is not removed from the silage in increased effluent. The opening of the plant cell wall polysaccharides caused by the breaking of some of the non-cellulosic polysaccharides allows the hitherto tightly-bound cellulose molecules to take up increasing numbers of water molecules, thus preserving the integrity of the materials in the silage and increasing the nutritive value with respect to control silages prepared without the addition of enzymes.

This process has a very important additional advantage: the removal of the non-cellulosic polysaccharides and the concomitant exposure of the loosened cellulose molecules will permit an increased rate of breakdown, upon ingestion by ruminants. Thus, with good palatability, the preservation of lactic acid and other plant cell fluids in the clamp, and an increased rate of cellulosic degradation in the rumen, silage made in this way will result in both increased feed intakes and increased nutritive value over untreated materials. This may be demonstrated by increases in values for digestibility determined in the laboratory; however, the important advantages will remain and be seen in increased nutritional values, as measured in the live animal.

It is also advantageous if plants containing a considerable quantity of carbohydrate are ensiled with the novel formulation which will convert sugars, whether endogenous or released by enzymes, to lactic acid. The conversion lowers the content of readily-available fermentable sugars, thus reducing the chances of subsequent spoilage due to aerobic fungal or yeast fermentation. This, coupled with the rapid lowering of the pH achieved by the microorganisms, results in the preservation of palatability and the reduction of both spoilage and wastage of ensiled materials, and thus increases the nutrient value of the crop.

Silage is stored in a silage clamp, which may be a silo adapted for the purpose or, very often, a covered heap in a farmyard. During storage, it is important to minimise liquid loss, since this represents both a loss in nutrients and a source of pollution. Silage treated with a composition of the invention can have reduced liquid loss.

The novel formulation may be provided in any suitable form. If desired, the enzymes and microorganism(s) may be packaged separately, for mixture before use.

The following Examples illustrate the invention. In the Examples, reference is made to microorganisms that have been deposited, under the terms of the Budapest Treaty, at NCIMB, Aberdeen, Scotland. The deposited strains, their accession numbers and deposit dates are as follows:

Lactobacillus plantarum BTL136, NCIB 12422, 5 Mar. 1987;

Pediococcus pentosaceus BTL138, NCIB 12455, 17 Apr. 1987;

Pediococcus pentosaceus IA 38/90-1, NCIMB 40456, 7 Dec. 1990.

EXAMPLE 1

A formulation having β-1,4-xylanase, β-1,3-xylosidase, α-L-arabinofuranosidase and β-1,3-arabinosidase activity, but with no detectable β-1,4-glucanase or β-1,4-cellobiohydrolase activity, was mixed with Pediococcus pentosaceus IA 38/90-1. The resultant formulation was sprayed on maize, and subjected to quality control calculated to ensure the production of at least 2% of fermentable sugars (by wet weight) from the maize. The presence of each enzyme was assayed individually. The amount of the microorganism was chosen to provide $10^5$ bacteria per gram of forage.

The resultant formulation was used to inoculate ensiled maize.

Table 2 shows the results of a comparison of the fermentation and nutritional qualities of treated and untreated crop 30 days after ensiling (CP=crude protein; TDM=total dry matter; DCP=digestible crude protein; MADF=modified acid detergent fibre; DOMD=digestibility of organic matter in dry matter).

TABLE 2

|  | Treated | Untreated |
|---|---|---|
| Dry matter (%) | 30.62 | 32.72 |
| TDM (%) | 32.52 | 34.62 |
| pH | 3.75 | 3.80 |
| % total nitrogen | 0.438 | 0.413 |
| Ammonia (% N) | 0.024 | 0.024 |
| Ammonia (% total N) | 5.5 | 5.8 |
| CP (% TDM) | 8.0 | 7.7 |
| DCP (g/kg) | 41.2 | 39.0 |
| MADF (TDM) | 22.95 | 27.85 |
| DOMD | 73.6 | 69.1 |
| ME (MJ/kg) | 11.8 | 11.1 |
| Ash (%) | 4.39 | 4.77 |

Aerobic stability was also tested, by plotting total yeasts and moulds (as $\log_{10}$CFU/g) over a period of 6 days. The untreated silage showed a fast increase, from 5 to 9 on the plot, within 3 days, and then remained at this level. The treated silage showed an approximately linear rise, reaching a value of 7 after 6 days. This is an important factor, since an increase in yeasts and moulds represents a decrease in palatability.

Tests have also been conducted on dairy cattle, using the formulation of Example 1 on maize silage having a dry matter content of nearly 40%. The farmer first fed the untreated maize silage, and then switched to the treated silage after 3 days. Milk quality and production all then rose, as follows (with respect to target values, which were not reached during initial feeding):

Protein: immediate increase, to 6 kg/day after 18 days
Fat: increase after 6 days, to 6 kg/day after 18 days
Yield: increase after 7 days, to 100 liters after 18 days Further, despite the high dry matter, the face of the silage clamp remained stable throughout the 21-day feeding period.

EXAMPLE 2

The same enzyme combination as in Example 1, but also including $\beta$-amylase, was mixed with *Pediococcus pentosaceus* BTL138 and *Lactobacillus plantarum* BTL136. The resultant formulation contained was sprayed on rye grass, and subjected to quality control as in Example 1. The total amount of the given microorganisms was again $10^5$ bacteria/g forage.

In order to assess the effect of the formulation of Example 2, by comparative tests, the following Experiments 1 to 3 were conducted:

Experiment 1

The formulation was used to inoculate direct cut perennial rye grass having a dry matter content of 26.5% by weight, in 1000 tonne pits. Table 3 shows the results of a comparison of the fermentation and nutritional qualities of treated and untreated crop 30 days after ensiling.

The treated silage had a higher crude protein and a lower ammonia content than the untreated material. This suggests that the former had reduced proteolytic degradation during the fermentation. Both silages had good pH values, but the lactic acid content of the treated material was higher.

Experiment 2

The formulation was used to inoculate alfalfa (DM 45%) held in 100 mm×350 mm PVC mini-silos. Table 4 gives a comparison of the rate of pH reduction for treated and untreated forage. Each result is the mean of three replicates.

The treated material reached a stable pH much more rapidly than the untreated material. Even where conditions were such that untreated forage would ensile successfully, the treatment resulted in a more rapid fermentation.

Analogous results were obtained for oats cut at the early milk stage (DM 29.7%) and for Sudan grass (DM 26.6%).

Experiment 3

The formulation was used to inoculate primary growth perennial rye grass (DM 17%) held in 80 tonne pits. Table 5 is a comparison of the effect on fully-fermented silage, for forage treated, in this way and with a proprietary formic acid additive, and untreated forage. Analyses were made of core samples taken 39 days after ensiling.

Both treated samples had similar characteristics, i.e. lower pH and ammonia values than the untreated material, and higher lactic acid contents. There was also a tendency for the nutritional quality (crude protein, ME and D value) to be higher for the treated material. The forage of the invention exhibited as good a preservation of nutrient (and crop) as did that treated with formic acid, even in this fairly low dry matter material.

The same three silages were also tested for the volume of effluent liberated over 39 days. The formic acid-treated silage liberated 6300 liters of effluent; the untreated silage liberated 4600 liters; the silage of the invention liberated 3700. This represents an unexpected but significant advantage.

TABLE 3

|  | Treated | Untreated |
|---|---|---|
| DM (%) | 25.3 | 27.3 |
| pH | 3.8 | 4.0 |
| CP (% DM) | 11.9 | 10.2 |
| Ammonia (% total N) | 9.8 | 28.0 |
| DOMD (% DM) | 62.4 | 61.6 |
| Lactic acid (g/kg DM) | 90.23 | 76.80 |

TABLE 4

|  | pH | |
|---|---|---|
| Time (days) | Treated | Untreated |
| 0 | 6.2 | 6.2 |
| 1 | 6.2 | 6.3 |
| 2 | 5.2 | 5.7 |
| 4 | 4.8 | 5.3 |
| 7 | 4.7 | 5.2 |
| 90 | 4.6 | 4.8 |

TABLE 5

|  | Treated | Formic Acid | Untreated |
|---|---|---|---|
| DM (%) | 17.2 | 17.1 | 16.6 |
| pH | 3.6 | 3.6 | 3.9 |
| CP (% DM) | 12.3 | 12.0 | 11.7 |
| Ammonia (% total N) | 5.6 | 3.8 | 8.8 |
| MADF (% DM) | 35.1 | 36.3 | 37.1 |

TABLE 5-continued

|  | Treated | Formic Acid | Untreated |
|---|---|---|---|
| D value | 63.0 | 62.0 | 61.3 |
| ME (MJ/kg DM) | 10.0 | 9.9 | 9.8 |
| Lactic acid (g/kg DM) | 110.9 | 91.9 | 61.3 |

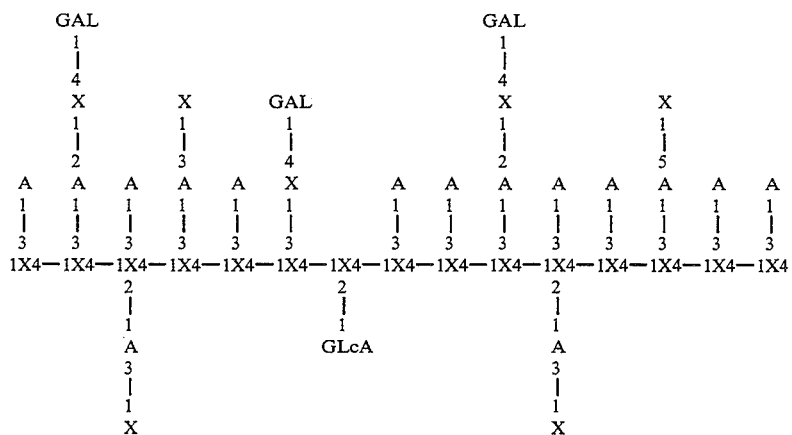

We claim:

1. A formulation consisting essentially of:
β-1,4-xylanase and β-1,3-xylosidase, but essentially free of β-1,4-glucanase and β-1,4-cellobiohydrolase; and
one or more lactic acid-producing bacteria selected for their ability to convert pentose to lactic acid, without degrading protein, at pH 4–6.5.

2. The formulation according to claim 1, additionally consisting essentially of α-L-arabinofuranosidase.

3. The formulation according to claim 2, additionally consisting essentially of β-1,3-arabinosidase.

4. The formulation according to claim 1, additionally consisting essentially of at least one enzyme selected from the group consisting of β-1,4-xylosidase, xylan endo-1,3β-xylosidase, β-L-arabinofuranosidase, β-1,3-arabinosidase, α-galactosidase, β-1,4-galactosidase, β-glucuronidase, α-amylase, polygalacturonase, pectin esterase, and pectin lyase.

5. The formulation according to claim 1, which additionally consisting essentially of pectinase.

6. The formulation according to claim 1, wherein each lactic acid-producing bacteria is additionally selected for its inability to degrade organic acids.

* * * * *